(12) United States Patent
Camden

(10) Patent No.: US 6,290,929 B1
(45) Date of Patent: Sep. 18, 2001

(54) CANCER TREATMENT

(75) Inventor: James Berger Camden, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/627,610

(22) Filed: Jul. 28, 2000

(51) Int. Cl.$^7$ ........................ A61K 31/53; C07D 253/075
(52) U.S. Cl. .................. 424/1.11; 424/94.63; 424/141.1; 424/649; 514/19; 514/21; 514/32; 514/34; 514/44; 514/56; 514/242; 544/182
(58) Field of Search ................................ 427/1.11, 94.63, 427/141.1, 649; 514/2.8, 19, 21, 32, 34, 44, 56, 242; 544/182

(56) References Cited

U.S. PATENT DOCUMENTS 3,077,473  2/1963  Liberman ............................ 544/182

OTHER PUBLICATIONS

Tennant et al. The Chemistry of Polyazaheterocyclic Compounds. . . J. Chem. Soc. Perkin Trans. I. pp. 421–428, 1976.*

* cited by examiner

*Primary Examiner*—Jeffrey E. Russel
(74) *Attorney, Agent, or Firm*—Rose Ann Dabek; Steven W. Miller

(57) ABSTRACT

This invention is a method of treating cancer, including carcinomas and sarcomas, through the administration of a pharmaceutical composition containing an arylaldehyde 5-oxo-1,2,4-triazine hydrazide derivative. The arylaldehyde 5-oxo-1,2,4-triazine hydrazide derivative is selected from the group consisting of those with the formula:

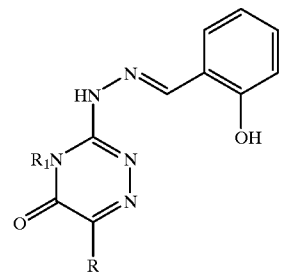

wherein R and $R_1$ are independently selected from the group consisting of hydrogen and alkyl wherein the alkyl group has up to 7 carbon atoms; or a pharmaceutical salt thereof; a prodrug thereof; a metabolite thereof; and mixtures thereof. Pharmaceutical compositions comprising these compounds and their use in various treatment methods are claimed. The compounds can be used in conjunction with other chemotherapeutic agents and potentiators.

37 Claims, No Drawings

CANCER TREATMENT

TECHNICAL FIELD

A method of treating cancer, including carcinomas and sarcomas is claimed. The pharmaceutical composition containing compounds is also claimed.

BACKGROUND OF THE INVENTION

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism of action of these chemotherapeutic agents is not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

The development of materials that would target tumor cells due to some unique specificity for them would be a breakthrough. Alternatively, materials that were cytotoxic to tumor cells while exerting mild effects on normal cells is also desirable.

SUMMARY OF THE INVENTION

A method of treating cancer, in particular, treating cancers in warm blooded animals and humans, comprising administering a therapeutically effective amount of a composition comprising one or more arylaldehyde 5-oxo-1,2,4-triazine hydrazide compounds selected from the group consisting of those having the formula:

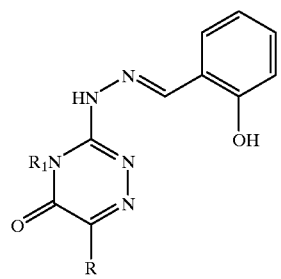

wherein R and R$_1$ are independently selected from the group consisting of hydrogen, or alkyl wherein the alkyl group has up to 7 carbon atoms. One or more of the pharmaceutical salts, metabolites and prodrugs of the arylaldehyde 5-oxo-1,2,4-triazine hydrazide compounds can also be used.

Preferably the compound is benzaldehyde, 2-hydroxy-, (4-hydro-5-oxo-1,2,4-triazin-3-yl)hydrazide which has the formula:

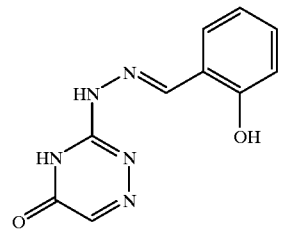

Referring to the generic structure, both R and R$_1$ are hydrogen. A second preferred compound is benzaldehyde, 2-hydroxy-, (4-hydro-5-oxo-6-methyl-1,2,4-triazin-3-yl) hydrazide that has the formula:

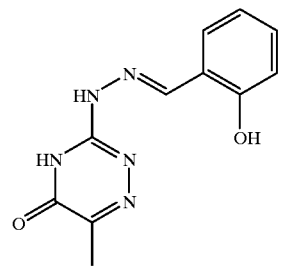

Referring to the generic structure, R is methyl and R$_1$ is hydrogen.

The present invention also provides a pharmaceutical composition comprising a pharmaceutically acceptable carrier and a therapeutically effective amount of a compound as described above.

These compositions have been discovered to inhibit the growth of cancer or other tumors in humans or animals by administration of a therapeutically effective amount of the composition, preferably by administering an arylaldehyde 5-oxo-1,2,4-triazine hydrazide compound to the site of the cancer.

More specifically, this invention provides an anti-cancer composition comprising a pharmaceutical carrier and arylaldehyde 5-oxo-1,2,4-triazine hydrazide derivative as defined herein along with a method for treating such cancers.

DETAILED DESCRIPTION OF THE INVENTION

A. DEFINITIONS

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, to shrink or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical salts" is salt of an arylaldehyde 5-oxo-1,2,4-triazine hydrazide derivative which has been modified by making acid or base salts of the compounds. Examples of pharmaceutically acceptable salts include, but are not limited to, mineral or organic acid salts of basic residues such as amines; alkali or organic salts of acidic residues such as phenols. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The preferred phenolate salts are the alkaline earth metal salts, sodium, potassium or lithium.

As used herein, a "pharmaceutical carrier" is a pharmaceutically acceptable solvent, suspending agent or vehicle, for delivering the arylaldehyde 5-oxo-1,2,4-triazine hydrazide compound to the animal or human. The carrier may be liquid or solid and is selected with the planned manner of administration in mind. Liposomes are also a pharmaceutical carrier.

As used herein, "cancer" refers to all types of cancer or neoplasm or malignant tumors found in mammals, including carcinomas and sarcomas. Examples of cancers are cancer of the brain, breast, cervix, colon, head & neck, kidney, lung, non-small cell lung, melanoma, mesothelioma, ovary, sarcoma, stomach, uterus and Medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with arylaldehyde 5-oxo-1,2,4-triazine hydrazide and optionally a potentiator and/or chemotherapeutic agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with arylaldehyde 5-oxo-1,2,4-triazine hydrazide and optionally a potentiator and/or another chemotherapeutic agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with arylaldehyde 5-oxo-1,2,4-triazine hydrazide and optionally a potentiator and/or a chemotherapeutic agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hürthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with arylaldehyde 5-oxo-1,2,4-triazine hydrazide according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

As used herein, the terms "arylaldehyde 5-oxo-1,2,4-triazine hydrazide derivative" and "arylaldehyde 5-oxo-1,2,4-triazine hydrazide compound" refer to one or more compounds having the generic formula:

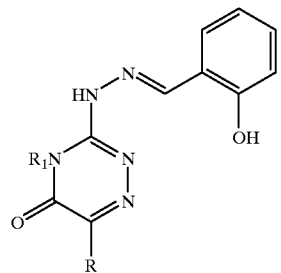

wherein R and $R_1$ are independently selected from the group consisting of hydrogen and alkyl wherein the alkyl group has up to 7 carbon atoms. The terms further include the pharmaceutical salts, metabolites and prodrugs of the arylaldehyde 5-oxo-1,2,4-triazine hydrazide derivative compounds of the above formula. More specific arylaldehyde 5-oxo-1,2,4-triazine hydrazide derivative compounds are described in detail below.

As used herein, the term "metabolite" refers to the breakdown or end product of a arylaldehyde 5-oxo-1,2,4-triazine hydrazide compound or its salt or prodrug produced by metabolism or biotransformation in the animal or human body; e.g., biotransformation to a more polar molecule such as by oxidation, reduction, or hydrolysis, or to a conjugate (see Goodman and Gilman "The Pharmacological Basis of Therapeutics" 8th ed., Pergamon Press, Gilman et al. (eds), 1990 for a discussion of biotransformation). As used herein, the metabolite of a arylaldehyde 5-oxo-1,2,4-triazine hydrazide derivative compound or its salt may be the biologically active form of the compound in the body. An assay for activity of a metabolite of a benzimidazole derivative of the present invention is known to one of skill in the art in light of the present disclosure, for example, testing for efficacy against a virus in vitro or in vivo.

By "alkyl" as used herein is meant a straight, branched or cyclic alkane derivatives.

As used herein "combination therapy" or "adjunct therapy" means that the patient in need of the drug is treated or given another drug for the disease in conjunction with one or more arylaldehyde 5-oxo-1,2,4-triazine hydrazide derivatives. This combination therapy can be sequential therapy where the patient is treated first with one drug and then the other or the two drugs are given simultaneously.

B. ARYLALDEHYDE 5-OXO-1,2,4-TRIAZINE HYDRAZIDE

The arylaldehyde 5-oxo-1,2,4-triazine hydrazide derivatives have the following structure:

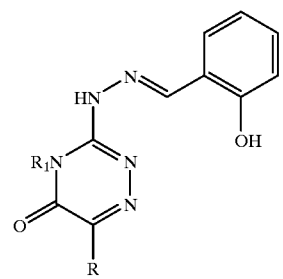

wherein R and $R_1$ are independently selected from the group consisting of hydrogen and alkyl wherein the alkyl group has up to 7 carbon atoms. Preferably the compounds have the formula:

Preferably the compound is benzaldehyde, 2-hydroxy-, (4-hydro-5-oxo-1,2,4-triazin-3-yl)hydrazide which has the formula:

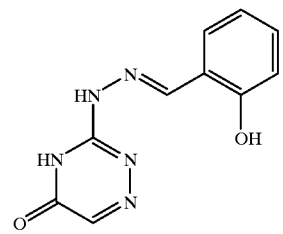

Referring to the generic structure, both R and $R_1$ are hydrogen. A second preferred compound is benzaldehyde, 2-hydroxy-, (4-hydro-5-oxo-6-methyl-1,2,4-triazin-3-yl) hydrazide that has the formula:

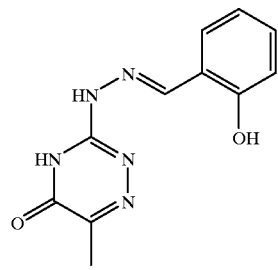

Referring to the generic structure, R is methyl and $R_1$ is hydrogen.

The arylaldehyde 5-oxo-1,2,4-triazine hydrazide compounds also include prodrugs. "Prodrugs" are considered to be any covalently bonded carriers which release the active parent drug according to the formula of the arylaldehyde 5-oxo-1,2,4-triazine hydrazide compound(s) described above in vivo when such prodrug is administered to a mammalian subject. Prodrugs of the arylaldehyde 5-oxo-1,2,4-triazine hydrazide compounds are prepared by modifying functional groups present in the compounds in such a way that the modifications are cleaved, either in routine manipulation or in vivo, to the parent compounds. Prodrugs include compounds wherein hydroxy or amine groups are bonded to any group that, when administered to a mammalian subject, cleaves to form a free hydroxyl or amino group, respectively. Examples of prodrugs include, but are not limited to, acetate, formate, or benzoate derivatives of alcohol and amine functional groups in the arylaldehyde 5-oxo-1,2,4-triazine hydrazide and phosphate esters, dimethylglycine esters, aminoalkylbenzyl esters, aminoalkyl esters and carboxyalkyl esters of phenol finctional groups in the arylaldehyde 5-oxo-1,2,4-triazine hydrazide; and the like.

The pharmaceutically acceptable salts of the arylaldehyde 5-oxo-1,2,4-triazine hydrazide include the conventional non-toxic salts or the quaternary ammonium salts of the arylaldehyde 5-oxo-1,2,4-triazine hydrazide formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention are synthesized from the arylaldehyde 5-oxo-1,2,4-triazine hydrazide derivative(s) which contain a basic moiety by conventional chemical methods. Generally, such salts are prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418.

Also included within the scope of the arylaldehyde 5-oxo-1,2,4-triazine hydrazide derivatives herein are active metabolites that are the break-down or final product of the arylaldehyde 5-oxo-1,2,4-triazine hydrazide derivatives, formed by metabolism or biotransformation in the animal or human body. The metabolite may be the biologically active form, rather than the benzimidazole derivative itself.

SYNTHESIS

The arylaldehyde 5-oxo-1,2,4-triazine hydrazide derivatives are prepared in a number of ways well known to one skilled in the art of organic synthesis. See for example, U.S. Pat. No. 3,077,473 issued to D. Libernan, 1963. See the following sequence.

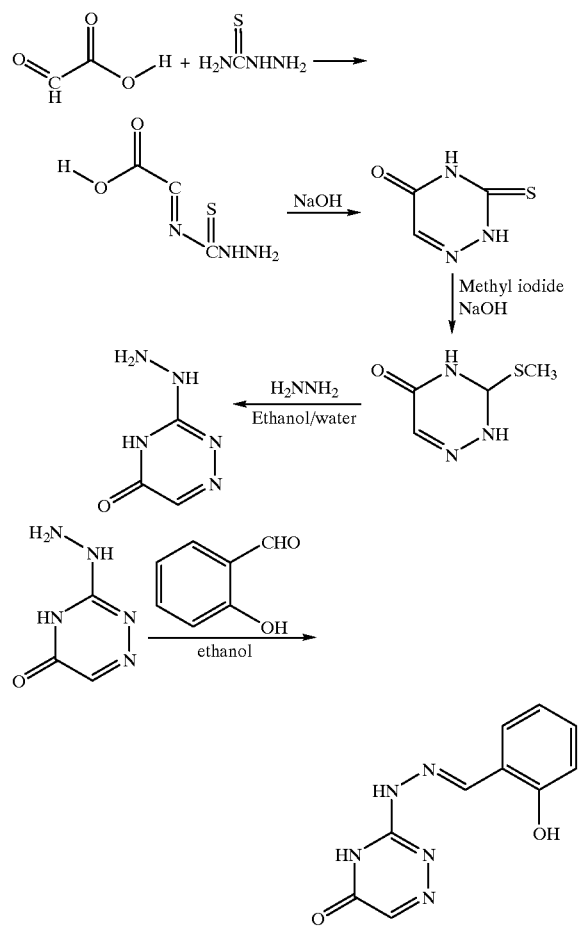

For example, 4-hydro-5-oxo-1,2,4-triazin-3-yl hydrazine can synthesized starting with glyoxylic acid as shown in the following reaction sequence. The resulting 3-(5-oxo-1,2,4-triazinyl) hydrazine is reacted with 2-hydroxybenzaldehyde or benzaldehyde in presence of a suitable organic solvent, for example a low molecular with alcohol to produce the corresponding hydrazide. In some cases an acid catalyst may also be used. Glyoxylic acid esters can be used. To make the substituted materials, analogs of glyoxylic acid are used. For example, pyruvic acid will yield the methyl derivative.

COMBINATION THERAPY

In some embodiments, arylaldehyde 5-oxo-1,2,4-triazine hydrazide is used in combination with one or more potentiators and/or chemotherapeutic agents for the treatment of cancer or tumors. An exemplary potentiator is triprolidine or its cis-isomer which are used in combination with chemotherapeutic agents and arylaldehyde 5-oxo-1,2,3-triazine hydrazide. Triprolidine is described in U.S. Pat. No. 5,114, 951 (1992). Another potentiator is procodazole, 1H-Benzimidazole-2-propanoic acid; [β-(2-benzimidazole) propionic acid; 2-(2-carboxyethyl)benzimidazole; propazol]. Procodazole is a non-specific immunoprotective agent active against viral and bacterial infections that is used with the compositions claimed herein. It is effective with arylaldehyde 5-oxo-1,2,4-triazine hydrazide in treating cancers, tumors or leukemia. Procodazole can also be combined with arylaldehyde 5-oxo-1,2,4-triazine hydrazide and other chemotherapeutic agents to treat cancer, tumor or leukemia.

Other potentiators which can be used with arylaldehyde 5-oxo-1,2,4-triazine hydrazide and optionally another chemotherapeutic agent to treat or inhibit the growth of cancer include monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl) ethylenediamine, leucovorin, heparin, N-[4-[(4-fluorphenyl) sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

The chemotherapeutic agents which can be used with arylaldehyde 5-oxo-1,2,4-triazine hydrazide and an optional potentiator are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with arylaldehyde 5-oxo-1,2,4-triazine hydrazide include members of all of these groups. For a detailed discussion of chemotherapeutic agents and their method of administration, see Dorr, et al, *Cancer Chemotherapy Handbook,* 2d edition, pages 15–34, Appleton & Lange (Connecticut, 1994).

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposde; and the DNA minor groove binder Plicamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa;

methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine.

DNA strand breaking agents include Bleomycin.

DNA topoisomerase II inhibitors include the following:

Intercalators, such as Amsacrine, Dactinomycin, Daunorubicin, Doxorubicin, Idarubicin, and Mitoxantrone; and nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine and Floxuridine purine antagonists such as Mercaptopurine, 6-Thioguanine, Pentostatin;

sugar modified analogs such as Cytarabine and Fludarabine; and ribonucleotide reductase inhibitors such as hydroxyurea.

Tubulin Interactive agents act by binding to specific sites on tubulin, a protein that polymerizes to form cellular microtubules. Microtubules are critical cell structure units. When the interactive agents bind on the protein, the cell cannot form microtubules. Tubulin Interactive agents include colchicine, Vincristine and Vinblastine, both alkaloids and Paclitaxel and cytoxan.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol; and androgens such as testosterone, testosterone propionate; fluoxymesterone, methyltestosterone.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamoxifen, antiandrogen agents such as Flutamide; and antiadrenal agents such as Mitotane and Aminoglutethimide.

Hydroxyurea, which appears to act primarily through inhibition of the enzyme ribonucleotide reductase, can also be used in combination with arylaldehyde 5-oxo-1,2,4 triazine hydrazide.

Asparaginase is an enzyme which converts asparagine to nonfunctional aspartic acid and thus blocks protein synthesis in the tumor. Asparaginase can also be used in combination with arylaldehyde 5-oxo-1,2,4-triazine hydrazide to treat cancer.

DOSAGE

Arylaldehyde 5-oxo-1,2,4-triazine hydrazide or its pharmaceutical salt or prodrug is preferably micronized or powdered so that it is more easily dispersed and solubilized by the body. Processes for grinding or pulverizing drugs are well known in the art. For example, a hammer mill or similar milling device are used. The preferred particle size is less than about 100µ and preferably less than 50µ.

Dosage forms (compositions) suitable for internal administration contain from about 1.0 milligram to about 5000 milligrams of active ingredient per unit. In these pharmaceutical compositions, the active ingredient will ordinarily be present in an amount of about 0.5 to about 95% by weight based on the total weight of the composition. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one pill will provide a dose of 25 mg per kg for that patient. It will provide a dose of only 12.5 mg/kg for a 80 kg patient.

By way of general guidance, for humans a dosage of as little as about 1 milligrams (mg) per kilogram (kg) of body weight and up to about 10000 mg per kg of body weight is suitable as a therapeutically effective dose. Preferably, from about 5 mg/kg to about 2500 mg/kg of body weight is used. Other preferred doses range between 25 mg/kg to about 1000 mg/kg of body weight. However, a dosage of between about 2 milligrams (mg) per kilogram (kg) of body weight to about 400 mg per kg of body weight is also suitable for treating some cancers.

Intravenously, the most preferred rates of administration may range from about 1 to about 1000 mg/kg/minute during a constant rate infusion. Arylaldehyde 5-oxo-1,2,4-triazine hydrazide may be administered in a single daily dose, or the total daily dosage may be administered in divided doses of two, three, or four times daily. Arylaldehyde 5-oxo-1,2,4-triazine hydrazide is generally given in one or more doses on a daily basis or from one to three times a week.

Arylaldehyde 5-oxo-1,2,4-triazine hydrazide is administered by any conventional means available for use in conjunction with pharmaceuticals, either as individual therapeutic agents or in combination with other therapeutic agents The amount and identity of a chemotherapeutic agent that is used with arylaldehyde 5-oxo-1,2,4-triazine hydrazide in treating cancer, tumor, leukemia, or other related diseases will vary according to patient response and physiology, type and severity of side effects, the disease being treated, the preferred dosing regimen, patient prognosis or other such factors.

When arylaldehyde 5-oxo-1,2,4-triazine hydrazide is used in combination with other therapeutic agents, the ratio of arylaldehyde 5-oxo-1,2,4-triazine hydrazide to the other therapeutic agent will be varied as needed according to the desired therapeutic effect, the observed side-effects of the combination, or other such considerations known to those of ordinary skill in the medical arts. Generally, the ratio of arylaldehyde 5-oxo-1,2,4-triazine hydrazide to other therapeutic agent will range from about 0.5%: 99.5% to about 99.5% : 0.5% on a weight basis.

When arylaldehyde 5-oxo-1,2,4-triazine hydrazide is administered before or after other therapeutic agents to treat cancer, tumors, or other diseases, the respective doses and the dosing regimen of arylaldehyde 5-oxo-1,2,4-triazine hydrazide and the other therapeutic agent may vary. The adjunct or combination therapy can be sequential, that is the treatment with one agent first and then the second agent, or it can be concomitant treatment wherein two or more agents are administered substantially at the same time. The sequential therapy can be within a reasonable time after the completion of the first therapy before beginning the second therapy. The treatment with both agents at the same time can be in the same daily dose or in separate doses. For example, treatment with one agent on day 1 and the other on day 2. The exact regimen will depend on the disease being treated, the severity of the disease and the response to the treatment.

For example, a full dosing regimen of arylaldehyde 5-oxo-1,2,4-triazine hydrazide can be administered either before or after a full dosing regimen of the other therapeutic agent, or alternating doses of arylaldehyde 5-oxo-1,2,4-triazine hydrazide and the other therapeutic agent may be administered. As a further example, arylaldehyde 5-oxo-1,2,4-triazine hydrazide can be administered concomitantly with the other therapeutic agent.

The identity of the chemotherapeutic agent, the pharmaceutical carrier and the amount of compound administered will vary widely depending on the species and body weight of mammal and the type of cancer being treated. The dosage administered will vary depending upon known factors, such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

Arylaldehyde 5-oxo-1,2,4-triazine hydrazide, the potentiator and/or the chemotherapeutic agent are administered together in a single dosage form or separately in two or more different dosage forms. These can be administered independently by the same route or by two or more different routes of administration depending on the dosage forms employed.

Suitable pharmaceutical compositions and dosage forms will preferably comprise arylaldehyde 5-oxo-1,2,4-triazine hydrazide, a potentiator and optionally a chemotherapeutic agent. The ratio of arylaldehyde 5-oxo-1,2,4-triazine hydrazide to potentiator is generally in the range of about 1:01 to 10:1, and preferably 1:.05 to 1:1 on a weight basis.

The dose and the range of chemotherapeutic agent will depend on the particular agent and the type of cancer being treated. One skilled in the art will be able to ascertain the appropriate dose.

DOSAGE FORM

A dosage unit may comprise a single compound or mixtures thereof with other anti-cancer compounds, other cancer or tumor growth inhibiting compounds. arylaldehyde 5-oxo-1,2,4-triazine hydrazide can be administered in oral dosage forms as tablets, capsules, pills, powders, granules, elixirs, tinctures, suspensions, syrups, and emulsions. Arylaldehyde 5-oxo-1,2,4-triazine hydrazide may also be administered in intravenous (bolus or infusion), intraperitoneal, subcutaneous, or intramuscular form, all using dosage forms well known to those of ordinary skill in the pharmaceutical arts.

Arylaldehyde 5-oxo-1,2,4-triazine hydrazide is typically administered in admixture with suitable pharmaceutical diluents, extenders, excipients, or carriers (collectively referred to herein as a pharmaceutically acceptable carrier or carrier materials) suitably selected with respect to the intended form of administration and as consistent with conventional pharmaceutical practices. The unit will be in a form suitable for oral, rectal, topical, intravenous injection or parenteral administration.

Arylaldehyde 5-oxo-1,2,4-triazine hydrazide can be administered alone but is generally mixed with a pharmaceutically acceptable carrier. This carrier can be a solid or liquid, and the type of carrier is generally chosen based on the type of administration being used.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Arylaldehyde 5-oxo-1,2,4-triazine hydrazide can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Arylaldehyde 5-oxo-1,2,4-triazine hydrazide may also be coupled to soluble polymers as targetable drug carriers or as a prodrug. Such polymers include polyvinylpyrrolidone, pyran copolymer, polyhydroxylpropylmethacrylamidephenol, polyhydroxyethylasparta-midephenol, or polyethyleneoxide-polylysine substituted with palmitoyl residues. Furthermore, arylaldehyde 5-oxo-1,2,4-triazine hydrazide may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Arylaldehyde 5-oxo-1,2,4-triazine hydrazide may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Useful pharmaceutical dosage forms for administration of arylaldehyde 5-oxo-1,2,4-triazine hydrazide are illustrated as follows:

Capsules

A large number of unit capsules are prepared by filling standard two-piece hard gelatin capsules each with 10 to 500 milligrams of powdered active ingredient, 5 to 150 milligrams of lactose, 5 to 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100–500 milligrams of the active ingredient. The capsules are washed and dried.

Tablets

A large number of tablets are prepared by conventional procedures so that the dosage unit was 100–500 milligrams of active ingredient, 0.2 milligrams of colloidal silicon dioxide, 5 milligrams of magnesium stearate, 50–275 milligrams of microcrystalline cellulose, 11 milligrams of starch and 98.8 milligrams of lactose. Appropriate coatings may be applied to increase palatability or delay absorption.

Injectable solution

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Kits

The present invention also includes pharmaceutical kits useful, for example, for the treatment of cancer, which comprise one or more containers containing a pharmaceutical composition comprising a therapeutically effective amount of arylaldehyde 5-oxo-1,2,4-triazine hydrazide. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The chemotherapeutic agents, arylaldehyde 5-oxo-1,2,4-triazine hydrazide and, optionally, the potentiators are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

D. METHOD OF TREATMENT

The method of treatment can be any suitable method that is effective in the treatment of the particular cancer or tumor type being treated. Treatment may be oral, rectal, topical, parenteral or intravenous administration or by injection into the tumor or cancer. The method of applying an effective amount also varies depending on the disorder or disease being treated. It is believed that parenteral treatment by intravenous, subcutaneous, or intramuscular application of arylaldehyde 5-oxo-1,2,4-triazine hydrazide, formulated with an appropriate carrier, additional cancer inhibiting compound or compounds or diluent to facilitate application will be the preferred method of administering the compounds to warm blooded animals.

One skilled in the art will recognize that the efficacy of the compounds can be ascertained through routine screening using known cancer cell lines both in vitro and in vivo. Cell lines are available from American Tissue Type Culture or other laboratories.

The following examples are illustrative and not intended to be limiting of the invention.

EXAMPLE 1

Each of the following compounds was tested for growth inhibition in a MTT assay against B16 Murine Melanoma and HT29 Colon Cancer, reported as $IC_{50}(\mu M)$.

| Compound | HT-29 $\mu$M | B16 $\mu$M |
|----------|------------|-----------|
| I        | 0.007      | 0.264     |
| II       | 0.019      | 1.1       |

Compound I is benzaldehyde, 2-hydroxy-, (4-hydro-5-oxo-1,2,4-triazin-3-yl)hydrazide which has the formula:

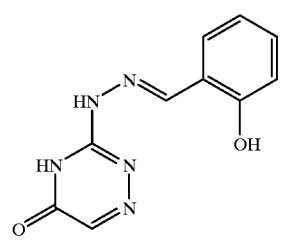

Compound II is benzaldehyde, 2-hydroxy-, (4-hydro-5-oxo-6-methyl-1,2,4-triazin-3-yl)hydrazide that has the formula:

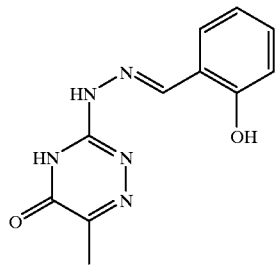

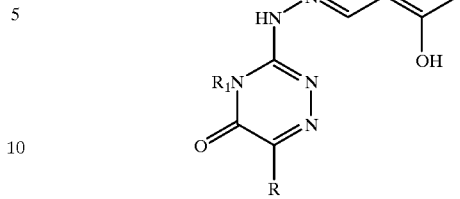

What is claimed is:

1. A method of treating cancer comprising administering to a patient in need thereof a therapeutically effective amount of a composition comprising a compound having the formula:

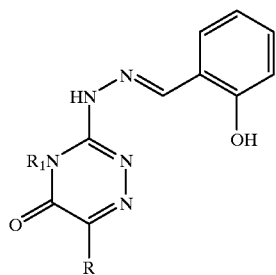

wherein R and $R_1$ are independently selected from the group consisting of hydrogen and alkyl
wherein the alkyl group has up to 7 carbon atoms;

or a pharmaceutical salt thereof; a prodrug thereof; a metabolite thereof; or mixtures thereof.

2. A method according to claim 1 wherein said cancer is prostate cancer.

3. A method according to claim 1 wherein said cancer is breast cancer.

4. A method according to claim 1 wherein said cancer is leukemia.

5. A method according to claim 1 wherein said cancer is pancreatic cancer.

6. A method according to claim 1 wherein said cancer is lung cancer.

7. A method according to claim 1 wherein said cancer is colon cancer.

8. A method according to claim 1 wherein said cancer is a sarcoma.

9. A method according to claim 1 wherein said cancer is a lymphoma.

10. A method according to claim 1 wherein R and $R_1$ each are hydrogen, or R is methyl and $R_1$ is hydrogen.

11. A pharmaceutical composition comprising a therapeutically effective amount of a composition comprising a compound having the formula:

wherein R and $R_1$ are independently selected from the group consisting of hydrogen and alkyl
wherein the alkyl group has up to 7 carbon atoms;

or a pharmaceutical salt thereof; a prodrug thereof; a metabolite thereof; or mixtures thereof.

12. A pharmaceutical composition of claim 11 further comprising a pharmaceutical carrier.

13. A pharmaceutical composition according to claim 12 further comprising a safe and effective amount of a potentiator.

14. A pharmaceutical composition according to claim 13, wherein said potentiator is selected from the group consisting of procodazole, triprolidine, propionic acid, monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, N-[4[(4-fluorphenyl)sulfonyl] phenyl] acetamide, leucovorin, heparin, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative having potentiator activity, and dimethyl sulfoxide.

15. A pharmaceutical composition according to claim 11 further comprising a safe and effective amount of a chemotherapeutic agent.

16. A pharmaceutical composition according to claim 15 wherein said chemotherapeutic agent is selected from the group consisting of a DNA-interactive agent, alkylating agent, antimetabolite, tubulin-interactive agent, and a hormonal agent.

17. A pharmaceutical composition according to claim 15 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole and Plicamycin.

18. A pharmaceutical composition according to claim 15 wherein said chemotherapeutic agent is selected from the group consisting of Methotrexate, Fluorouracil, Fluorodeoxyuridin, CB3717, Azacitidine, Floxuridine, Mercapyopurine, 6-Thioguanine, Pentostatin, Cytarabine, and Fludarabine.

19. A pharmaceutical composition according to claim 15 further comprising a safe and effective amount of a potentiator.

20. A pharmaceutical composition according to claim 19, wherein said potentiator is selected from the group consisting of procodazole, triprolidine, propionic acid, monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, N-[4-[(4-fluorphenyl)sulfonyl] phenyl] acetamide, leucovorin, heparin, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative having potentiator activity, and dimethyl sulfoxide.

21. A method of treating cancer comprising administering to a patient in need thereof a therapeutically effective amount of a compound having the formula:

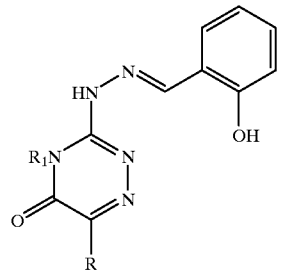

wherein R and $R_1$ are independently selected from the group consisting of hydrogen and alkyl
wherein the alkyl group has up to 7 carbon atoms;
or a pharmaceutical salt thereof; a prodrug thereof; a metabolite thereof; or mixtures thereof;
in a combination therapy with a safe and effective amount of a potentiator or a chemotherapeutic agent.

22. A method according to claim 21 wherein said cancer is a lymphoma.

23. A method according to claim 21 wherein said cancer is a sarcoma.

24. A method according to claim 21 wherein R and $R_1$ each are hydrogen, or R is methyl and $R_1$ is hydrogen.

25. A method according to claim 21 wherein said combination therapy is with a chemotherapeutic agent and the chemotherapeutic agent is selected from the group consisting of a DNA-interactive agent, an alkylating agent, an antimetabolite, a tubulin-interacive agent, and a hormonal agent.

26. A method according to claim 21 wherein said combination therapy is with a chemotherapeutic agent and the chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole and Plicamycin.

27. A method according to claim 21 wherein said combination therapy is with a chemotherapeutic agent and the chemotherapeutic agent is selected from the group consisting of Methotrexate, Fluorouracil, Fluorodeoxyuridine, CB3717, Azacitidine, Floxuridine, Mercaptopurine, 6-Thioguanine, Pentostatin, Cytarabine, and Fludarabine.

28. A method according to claim 21 wherein said combination therapy is with a safe and effective amount of a potentiator.

29. A method according to claim 21, wherein said potentiator is selected from the group consisting of procodazole, triprolidine, propionic acid, monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dmethoxybenzyl)ethylenediamine, N-[4-[(4[fluorphenyl)sulfonyl]phenyl] acetamide, leucovorin, heparin, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative having potentiator activity, and dimethyl sulfoxide.

30. A liposome composition comprising a compound having the formula:

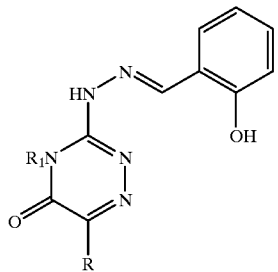

wherein R and $R_1$ are independently selected from the group consisting of hydrogen and alkyl
wherein the alkyl group has up to 7 carbon atoms;
or a pharmaceutical salt thereof; a prodrug thereof; a metabolite thereof; or mixtures thereof.

31. A liposome composition according to claim 30 wherein the liposome is selected from the group consisting of unilamellar vesicles and multilamellar vesicles.

32. A liposome composition according to claim 30 formed from a phospholipid, cholesterol, or stearylamine.

33. A pharmaceutical composition comprising the hydrochloride salt of a compound having the formula:

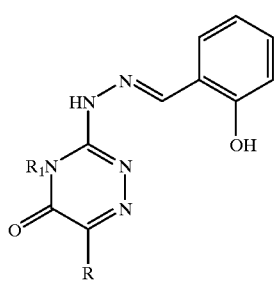

wherein R and $R_1$ are hydrogen, or R is methyl and $R_1$ is hydrogen.

34. A pharmaceutical composition according to claim 33 in an injectable form.

35. The liposome composition according to claim 32 formed from a phospholipid and the phospholipid is phosphatidyl choline.

36. A method according to claim 1 wherein the cancer is melanoma.

37. A method according to claim 1 wherein the cancer is a carcinoma.

* * * * *

UNITED STATES PATENT AND TRADEMARK OFFICE
CERTIFICATE OF CORRECTION

PATENT NO.   : 6,290,929 B1
DATED        : September 18, 2001
INVENTOR(S)  : James Berger Camden It is certified that error appears in the above-identified patent and that said Letters Patent is hereby corrected as shown below:

Column 18,
Line 56, delete "Fluorodeoxyuridin" and insert therefor, -- Fluorodeoxyuridine --.
Line 57, delete "Mercapyopurine" and insert therefor, -- Mercaptopurine --.

Column 19,
Line 61, delete "21" and insert therefor, -- 28 --.

Column 20,
Line 3, delete "3,4-dmethoxybenzyl" and insert therefor, -- 3,4-dimethoxybenzyl --.

Signed and Sealed this

Twenty-fifth Day of June, 2002

*Attest:*

*Attesting Officer*

JAMES E. ROGAN
*Director of the United States Patent and Trademark Office*